(12) United States Patent
Jansen et al.

(10) Patent No.: US 10,022,151 B2
(45) Date of Patent: Jul. 17, 2018

(54) EASY GLIDE ABRASIVE TIP FOR A MICRODERMABRASION DEVICE

(71) Applicant: KONINKLIJKE PHILIPS N.V., Eindhoven (NL)

(72) Inventors: Marjolein Yvonne Jansen, Eindhoven (NL); Eelco Henricus Maria Bruin, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 177 days.

(21) Appl. No.: 14/893,563

(22) PCT Filed: Apr. 30, 2014

(86) PCT No.: PCT/EP2014/058826
§ 371 (c)(1),
(2) Date: Nov. 24, 2015

(87) PCT Pub. No.: WO2014/191149
PCT Pub. Date: Dec. 4, 2014

(65) Prior Publication Data
US 2016/0106468 A1    Apr. 21, 2016

(30) Foreign Application Priority Data

May 30, 2013    (EP) .................................... 13169836

(51) Int. Cl.
*A61B 17/54*  (2006.01)
*A61H 9/00*   (2006.01)
(Continued)

(52) U.S. Cl.
CPC .............. *A61B 17/54* (2013.01); *A61B 17/32* (2013.01); *A61H 7/005* (2013.01); *A61H 7/008* (2013.01);
(Continued)

(58) Field of Classification Search
CPC .............. A61H 7/008; A61B 2017/308; A61B 2017/00761; A61B 2017/32004; A61B 2017/005
See application file for complete search history.

(56) References Cited

U.S. PATENT DOCUMENTS 5,100,412 A    3/1992  Rosso
6,090,055 A *  7/2000  Frajdenrajch .......... A61H 7/008
                                                  15/344

(Continued)

FOREIGN PATENT DOCUMENTS

JP    6069091 B2    1/2017
WO    0141651 A2    6/2001

OTHER PUBLICATIONS

Influence of Surface Roughness, Material and Climate Conditions on the Friction of Human Skin, C.P. Hendriks & S.E. Franklin, Tribol Letters (2010) 37:361-373.

*Primary Examiner* — Alexander Orkin

(57) ABSTRACT

The invention provides a microdermabrasion device comprising a vacuum system and a device tip, wherein the vacuum system comprises a channel with a channel inlet at the device tip, wherein the channel inlet is surrounded by a channel rim which facilitates gliding of the device tip over a skin, and wherein the device tip comprises a microdermabrasion zone configured remote from the channel inlet with a recession configured between the microdermabrasion zone and the channel rim.

10 Claims, 4 Drawing Sheets

(51) Int. Cl.
   *A61B 17/32* (2006.01)
   *A61H 7/00* (2006.01)
   *A61B 17/00* (2006.01)
   *A61B 17/30* (2006.01)

(52) U.S. Cl.
   CPC .. *A61H 9/0057* (2013.01); *A61B 2017/00561* (2013.01); *A61B 2017/00761* (2013.01); *A61B 2017/308* (2013.01); *A61B 2017/320004* (2013.01); *A61B 2217/005* (2013.01); *A61H 2201/0107* (2013.01)

(56) References Cited

U.S. PATENT DOCUMENTS

| | | |
|---|---|---|
| 6,241,739 B1 | 6/2001 | Waldron |
| 6,299,620 B1 | 10/2001 | Shadduck |
| 6,641,519 B1 | 11/2003 | Kindlein |
| 6,641,591 B1* | 11/2003 | Shadduck .............. A61B 17/54 606/131 |
| 6,911,031 B2 | 6/2005 | Muldner |
| 6,926,681 B1 | 8/2005 | Ramey |
| 7,153,311 B2 | 12/2006 | Chung |
| 8,226,663 B2 | 7/2012 | Remsburg |
| 8,236,008 B2 | 8/2012 | Boone, III |
| 8,337,513 B2 | 12/2012 | Shadduck |
| 2002/0058856 A1* | 5/2002 | Peng ...................... A61B 17/02 600/37 |
| 2003/0139644 A1* | 7/2003 | Parsons .................. A61B 17/02 600/37 |
| 2003/0187462 A1 | 10/2003 | Chang |
| 2003/0229369 A1* | 12/2003 | Findlay, III .... A61B 17/320758 606/159 |
| 2006/0253125 A1 | 11/2006 | Ignon |
| 2006/0276806 A1 | 12/2006 | Martinez Zunino |
| 2007/0005078 A1 | 1/2007 | Hart |
| 2007/0010828 A1* | 1/2007 | Eknoian ................. A61B 17/54 606/131 |
| 2007/0156124 A1* | 7/2007 | Ignon ................... A61B 17/545 606/9 |
| 2012/0136374 A1 | 5/2012 | Karasiuk |
| 2013/0158547 A1* | 6/2013 | David .................... A61B 18/14 606/41 |

* cited by examiner

EASY GLIDE ABRASIVE TIP FOR A MICRODERMABRASION DEVICE

This application is the U.S. National Phase application under 35 U.S.C. § 371 of International Application No. PCT/EP2014/058826, filed on Apr. 30, 2014, which claims the benefit of European Application No. 13169836.7 filed on May 30, 2013. These applications are hereby incorporated by reference herein.

FIELD OF THE INVENTION

The invention relates to a microdermabrasion device, to a method for the controlled removal of at least part of the stratum corneum with such device, as well as to specific uses of such device.

BACKGROUND OF THE INVENTION

Microdermabrasion devices are known in the art. U.S. Pat. No. 6,241,739 describes for instance a treatment tool and tissue collection system, for removal of outer layers of skin to provide a revitalized, fresh skin surface, and a method of using same, comprising an abrasive tipped tool mounted on the end of a tube, said tube being connected to a source of vacuum. The vacuum aids in maintaining intimate contact between the abrasive tip and the skin during the treatment process and transports the removed tissue to a collection container.

Especially, this document describes a device for removing portions of the outer layers of skin comprising a source of a vacuum, and a tube with an abrasive treatment tip thereon for dislodging cells from a surface being treated, the tube being attached to the source of vacuum so that a lumen through the tube has a reduced pressure therein which is less than the ambient pressure surrounding the tube, the abrasive treatment tip having at least one opening therein for applying the reduced pressure within the tube to a skin surface, said vacuum causing the skin being treated to have an increased area of contact with the abrasive tip, the vacuum also functioning to collect tissue or cells removed from the skin surface being treated.

Further, this document describes a method of treating the skin surface of a patient to remove surface cells and reduce undesirable skin blemishes comprising providing a tubular treatment tool with an abrasive skin contacting surface, providing a pressure through a lumen within the tubular treatment tool which is less than ambient pressure surrounding the treatment tube, and bringing the abrasive skin contacting surface into contact with the skin surface to be treated while said lesser pressure is delivered to the skin surface through the lumen and moving the abrasive skin contacting surface across the skin surface.

U.S. Pat. No. 6,299,620 describes a system for atraumatic removal of skin surface layers in a treatment to induce neocollagenesis in the dermis to reduce wrinkles and alter the architecture of the dermal layers. An embodiment comprises (i) a hand-held instrument with a resilient working skin interface that carries microscopic diamond fragments for abrading the skin surface in a controlled manner; (ii) a fluid source for supplying sterile fluids to the skin interface for cleaning skin debris from the skin interface; and (iii) a negative pressure source for pulling fluid to the skin interface and thereafter aspirating fluid and skin debris from a treatment site. The skin interface is formed of a resilient material such as silicone to allow the working end to flex and atraumatically engage the skin surface as it is translated across a treatment site. The system also carries a disposable cartridge filled with fluid in the hand-held instrument.

U.S. Pat. No. 6,641,591 describes an instrument and technique for the removal of epidermal layers in a controlled manner utilizing a hand-held instrument with a working end that (i) a vacuum aspiration system, (ii) a source for delivery of a sterile fluids or pharmacological agents to the skin; and (iii) a skin interface surface in the working end that has specially shape structure for abrading surface layers of the patient's epidermis as the working end is moved over the patient's skin while at the same time causing rapid penetration of the fluids into the skin for therapeutic purposes.

US2007005078 describes a system for abrading skin to remove outer portions thereof includes an apparatus having a skin abrading head with a head portion and a skin abrading brush. The outer head portion has a rim for placement in contact with the skin along with the bristles of the brush. Air flow is generated in the head to bring the skin into engagement with the rim and bristles and transport removed skin portions.

US2003187462 describes a tissue removal pen which includes a pen body having a working end and a handle portion, and an abrasion unit, which is mounted on the pen body, including an abrasion head extended outwardly from the working end of the pen body for removing cells from a treating skin surface of a user. A collecting unit includes a collecting conduit, which is mounted on the pen body, having a discharging end and an intake end extended toward the working end, and a collecting head replaceably mounted to the intake end of the collecting conduit and extended from the working end of the pen body to a position that adjacent to the abrasion head of the abrasion unit. A vacuuming source is connected to the discharging end of the collecting conduit to provide a reduced pressure within the collecting head for collecting cells removed from the treating skin surface.

WO0141651 describes a treatment tool and tissue collection system, for removal of outer layers of skin to provide a revitalized, fresh skin surface, and a method of using same, comprising an abrasive tipped tool mounted on the end or within the end of a hollow tube, said tube being connected to a source of vacuum. The vacuum aids in maintaining intimate contact between the abrasive tip and the skin during the treatment process and transports the removed tissue to a collection container. The abrasive surface within the tube is a motor driven abrasive pad. Contact between the pad and the abrasive disk is brought about or increased by application of a vacuum through the tube to the skin surface.

SUMMARY OF THE INVENTION

The "micro dermo abrasion" or "mircodermabrasion" (MDA) technique is being used to help the upper skin layer (the so called stratum corneum) to renew in a faster way than it would normally do. Traditionally, crystal microdermabrasion system contains a pump, a connecting tube, a hand piece, and a vacuum source. While the pump creates a high-pressure stream of inert crystals, like aluminum oxide, to abrade the skin, the vacuum removes the crystals and exfoliated skin cells. Instead of abrasion with particles in a gas stream, also a roughened surface, such as a diamond surface, of the tip of the device can be used. This is for instance known as (diamond) microdermabrasion. Unlike the crystal microdermabrasion system, the (diamond) microdermabrasion does not produce particles from crystals that may be inhaled into patients' nose or blow into the eyes. The present invention especially relates amongst others to a microdermabrasion device with a stationary abrasion zone (i.e. no moving abrasive part) and to microdermabrasion devices which use the abrasion zone as abrasive means, thus without the use of abrasive particles that are used to abrade the skin and may be sucked by the vacuum. However, in other embodiments, the present invention also relates to a microdermabrasion devices wherein the microdermabrasion zone may be moving (i.e. not stationary).

Prior art devices may not have an optimized balance between abrasion effectiveness and easiness in use. Lowering a vacuum in device allows the user to move with less force over the skin but reduces effectiveness. Increasing the vacuum may improve effectiveness, but may make it more difficult to move over the face and/or may reduce application comfort. Further, increasing the friction/abrasion of the abrasive texture may reduce application comfort. Likewise, reducing the friction/abrasion of the abrasive texture may improve gliding over the face, but may reduce effectiveness.

Hence, it is an aspect of the invention to provide an alternative micro-dermabrasion device, which preferably further at least partly obviates one or more of above-described drawbacks. Further, it is an aspect of the invention to provide an alternative method for the controlled removal of at least part of the stratum corneum, which preferably further at least partly obviates one or more of above-described drawbacks.

Surprisingly, it has been found that by a specific geometry the gliding force can be reduced and/or the treatment area can be increased with the same gliding force. Especially, the invention provides two zones, especially two rings, of which one zone provides the abrasive function and of which one zone provides a gliding function (to facilitate gliding over the skin). For instance, two zones, especially two rings, may be configured around the vacuum opening. The inner zone, especially the ring, around the vacuum opening is the gliding zone (or especially the gliding ring). It has substantially no abrasion/abrasive function and may be smooth. Hence, this zone, especially the ring, facilitates gliding of the device tip over a skin (of a human). The outer zone, especially the ring, is the abrasive zone. Hence, this zone, especially the ring, may have abrasive roughness. The roughness and sharpness of the abrasive texture may depend on the treatment goal and personal preferences of users. Hence, this zone, especially the ring, is configured to provide the abrasive function for the controlled removal of at least part of the stratum corneum. In between the two zones, especially in between the rings, there is an area that is further away from the skin. This area separates the two zones, especially the rings. The invention is not limited to ring-like microdermabrasion zones and/or ring-like channel rims (or gliding zones).

The gliding zone, especially the ring (especially the inner ring), may be needed for easy gliding over the skin, which will make the device easy to use. Friction can be tuned by (ring) shape, material roughness, material type, surface topography, coatings and other friction reduction methods. Lowering vacuum level also helps reducing friction, but this may be less desired because this limits the benefits (see also above). The outer zone, especially the (outer) ring, contains the abrasive texture. Abrasiveness can be tuned by texture sharpness, texture roughness, material type, ring shape, ring height, etc. The area in between the zones, especially the rings, which is further away from the skin, has an important function. It separates the gliding area from the abrasive area. It may further gives pressure to the gliding zone which may need pressure to be able to close the vacuum opening on the skin. It seems that there may be a non-linear relation between abrasion and vacuum whereas in prior art systems there may be a linear relation. This has the advantage that abrasion and vacuum can better be optimized. Hence, the device may have two zones with two different functions: vacuum is one of the main functions as it may also improve skin regeneration. The vacuum effect becomes bigger when a higher vacuum setting is used or when the vacuum opening is larger. The amount of abrasion is amongst others dependent on the sharpness of the abrasive texture and the roughness of the structure. Gliding is important to make it possible for the tip to move easy over the face and to treat the face exactly the way the user wants. Gliding is easy when the friction is low. Vacuum may increase the friction. This cannot be avoided without losing the benefits of vacuum. Another factor which may increase the friction is the abrasion due to interlocking skin. This function is needed for mentioned the benefits. However the friction can be lowered if the pressure on the abrasive is less. By placing the abrasive zone, especially the ring (or other shaped microdermabrasion zone), outside the vacuum area, the pressure on it may be lower. The friction of the abrasive zone, may therefore be lower and therefore the gliding of the tip is improved. The amount of pressure should be enough for reaching abrasion benefits.

Further, the present device does not need to use liquids with abrasive material. This may add to the ease of use and the life time of the device.

Hence, in a first aspect the invention provides a microdermabrasion device ("device" or "MDA device") comprising a vacuum system and a device tip ("tip"), wherein the vacuum system comprises a channel with a channel inlet at the device tip, wherein the channel inlet is (perimetrically) surrounded by a channel rim ("rim"), which is especially configured to facilitate gliding of the device tip over a skin (especially of a human), and wherein the device tip comprises a microdermabrasion zone ("abrasion zone" or "abrasive zone") configured remote from the channel inlet with a recession ("recession") configured between the microdermabrasion zone and the channel rim. Especially, the channel inlet is perimetrically surrounded by a channel rim, and wherein the microdermabrasion zone perimetrically surrounds the channel rim. As indicated further below, such configuration may allow a larger treatment (abrasion) area than conventional devices and/or allows a less vacuum. Hence, the device may provide a faster and/or more convenient treatment of the skin, with similar or even better abrasion results. In conventional device, as better treatment may always imply a higher vacuum, which is inconvenient for the user. Further, there is no necessity to use a liquid or to use moving abrasive particles.

In yet a further aspect, the invention also provides a method for the controlled removal of at least part of the stratum corneum, the method comprising contacting the microdermabrasion device, such as defined herein, with part of a skin and removing at least part of the stratum corneum while applying a vacuum to the vacuum channel.

As indicated above, the microdermabrasion device comprises a tip, of which at least part is in contact with the skin when the device is being applied. It is also this part, where the abrasion zone is located and where the channel inlet is located. The channel inlet is that part of the device tip that sucks the skin and thereby promotes keeping skin contact. The vacuum system, the channel inlet and the channel rim (see also below), may facilitate sucking the skin (slightly) into the channel opening. The advantages thereof are massage of the skin, improving contact of the device tip with the skin and also removal of debris (i.e. exfoliated skin cells).

The vacuum system may comprise a source of vacuum, such as pump, configured to provide a suction flow in a direction from the channel inlet to the source of vacuum, such as a pump. The channel inlet, which is at the device tip, is thus configured upstream of the vacuum pump. Especially, the device may be configured to provide a negative pressure in the range of 5-80 kPa, such as especially 15-60 kPa, such as in the range of 20-40 kPa. This may especially imply that when the skin is in contact with the channel outlet, and closes off the channel outlet, the device is able to provide a pressure which is in the range of 15-60 kPa lower than atmospheric pressure. Hence, debris from the skin, removed with the MDA device is sucked via the channel inlet, and via the channel, in the direction of the pump.

In general, the channel inlet or channel opening is configured in such a way, that a good closing connection with the skin may be achieved. Especially, the channel opening comprises a rim, herein also indicated as "channel rim". This channel rim may be a (slightly) protruding part of the device tip. The channel rim may also be seen as a distal part or end part of the channel opening. Especially this rim will be in contact with the skin of a user during use of the device.

The channel rim may have different shapes, but is especially configured to (perimetrically) surround the channel inlet. This rim may have a ring shape, which may substantially be round. However, the rim may also have a distorted ring shape, such as an elliptical ring shape (oval). Also other shapes may be possible, like a non-circular or non-oval shape. However, especially, the entire channel inlet is over its entire perimeter surrounded with such rim. Hence, the invention also provides an embodiment of the microdermabrasion device, wherein the channel rim has a round ring shape, wherein the recession has a round ring shape, and wherein the microdermabrasion zone has a round ring shape. However, the invention also provides an embodiment of the microdermabrasion device, wherein the channel rim has an oval ring shape, wherein the recession has an oval ring shape, and wherein the microdermabrasion zone has an oval ring shape. However, combinations are also possible, such as a round channel rim and an oval microdermabrasion zone. Especially an oval shape appears to be convenient for users.

As indicated above, this channel rim especially has substantially no abrasive properties, but is configured to facilitate gliding of the device tip over the skin (of a human). Hence, the rim may have a relative smooth surface. The channel rim may also be indicated as gliding rim, such as a gliding ring. Especially, the channel rim has no sharp edges, and may be rounded off.

Further, the device comprises a microdermabrasion zone ("abrasion zone"). This zone is configured at some distance of the channel inlet. The channel rim may provide an edge to the channel inlet and the abrasion zone is configured remote from this rim and channel inlet. Especially, between the channel rim and this abrasion zone there is some distance, more particular there is a recession, indicated as recession, in between. Hence, the channel rim and abrasion zone are elevated relative to this recession. This physical different arrangement facilitates the separation of the two functions: gliding and abrading. The abrasion zone may at least partly surround the channel rim, but does not necessarily entirely surround it. However, in a specific embodiment the microdermabrasion zone (perimetrically) surrounds the channel rim with the recession configured between the microdermabrasion zone and the channel rim. As indicated above, the channel rim may have a ring shape. Hence, in a further specific embodiment the channel rim has a ring shape, wherein the recession has a ring shape, and wherein the microdermabrasion zone has a ring shape, with the microdermabrasion zone surrounding the channel rim with the recession configured between the microdermabrasion zone and the channel rim.

Note that the term "(perimetrically) surrounding" does include shapes that are round, square, rectangular, elliptical (oval), etc. etc. The term "ring" herein especially indicate a round or elliptical ring, even more especially a round ring. The use of a perimetrically surrounding rim and/or a perimetrically surrounding abrasion zone refers to rims or zones In a specific embodiment, the recession has a recession bottom, wherein the channel rim has relative to the recession bottom a channel rim height, wherein the microdermabrasion zone has relative to the recession bottom a microdermabrasion zone height. Especially, the channel rim height and the microdermabrasion zone height have a height difference in the range of 0-5 mm, such as up to 2 mm. Hence, the height difference can be zero, i.e. equal height, up to 5 mm (lower or higher), such as up to 3 mm, like up to 2 mm. Hence, the rim may e.g. be 2 mm lower or higher than the microdermabrasion zone. Though the channel rim and the abrasion zone may have the same height (height difference is zero), especially there is a height difference, such as in the range of 0-5 mm. Larger or smaller difference may not lead to the desired function of vacuum and abrasion, and/or to the desired separation of these functions. Note that in a first embodiment the channel rim is higher than the abrasion zone, i.e. when moving the tip to the skin, the channel rim will in principle first touch the skin. Hence, in an embodiment the channel rim height (h1) is larger than the microdermabrasion zone height (h2). However, in a second embodiment the abrasion zone is higher than the channel rim, i.e. when moving the tip to the skin, the abrasion zone will in principle first touch the skin. Hence, in an embodiment the height difference is zero and in another embodiment, the height difference is non-zero, such as larger than zero mm and equal to or smaller than 5 mm. An advantage of the tunability of the height differences is that thereby the pressure (on the skin) of the abrasive zone can be tuned. In this way, the device can be adapted to different applications. Optionally, the device is configured to allow adaption of the height difference by the user (e.g. by a turning motion). In another embodiment, the height difference is fixed (especially set during production)(which height difference may, as indicated above, be zero or non-zero).

Especially, the rim is higher than the microdermabrasion zone, though a slightly lower rim may also be possible. Especially, the height difference is in the range of −5-+5 mm, such as −2-+5 mm, especially in the range of −1-+2 mm. Especially, the rim is higher than the microdermabrasion zone, such as at least 0.2 mm higher, especially at least 0.35 mm higher. Especially with these height differences, good results are obtained with respect to a relative large microdermabrasion zone and/or a relative moderate vacuum. The phrase "wherein the height difference is in the range of "−2-+5 mm" or "a height difference of at least 0.2 mm", and similar phrases indicted that the rim or gliding zone is higher than the microdermabrasion with the indicated value. Hence, a value of −2 mm indicated that the rim is 2 mm lower than the microdermabrasion zone, whereas a value of +5 mm indicates that the rim of gliding zone is 5 mm higher than the microdermabrasion zone.

Especially, the channel opening (with its channel rim) is configured such that a suitable vacuum area is obtained. Especially, the channel rim has (or provides) a vacuum area in the range of 10-400 mm$^2$, such as 10-200 mm$^2$, like 45-75 mm², such as especially 50-75 mm². This vacuum area is especially the area enclosed by the channel rim.

As indicated above, the abrasion zone has abrasive properties, such as due to microscopic structures that facilitate abrasion of the upper part of the skin. Such microscopic structures may for instance be selected from the group consisting of alumina structures, such as particles, and diamond structures, such as diamond particles. These structures are comprised by the abrasion rim, i.e. are attached or part of the rim. Especially, the microdermabrasion zone comprises abrasive structures, such as particulate material, attached to the microdermabrasion zone having mean dimensions in the range of 1-1000 µm, such as 2-300 µm, like 5-80 µm or 120-200 µm. Alternatively or additionally, the microscopic structures may for instance be selected from the group consisting of silicon carbide structures, such as silicon carbide particles, and metal nitride structures, such as metal nitride particles. Alternatively or additionally, the microscopic structures may for instance be selected from the group consisting of metal oxide structures, such as aluminum oxide particles and aluminum oxide structures. Further options of microscopic structures may for instance be selected from the group consisting of diamond structures, boron nitride structures, silicon carbide structures (see also above), glass beads, steel grit structures, other metal grit structures, zirconium oxide structures, and quartz structures. Combinations of different kind of structures, both in chemical composition and/or dimensions, may also be applied. In an embodiment, the quotient of the number of abrasive particles at the channel rim is especially 10% or less, more especially 5% or less, even more especially 1% or less of the number of abrasive particles comprised by the microdermabrasion zone, especially 0.1% or less. In an embodiment, such abrasive particles are not comprised at all by the channel rim. The lower content or absence of such particles by the channel rim may facilitate gliding. The numbers given here as especially provided as an indication for certain embodiments to indicate the difference between the functionality of the channel rim and the microdermabrasion zone.

The abrasive particles are especially available in the microdermabrasion zone in a density in the range of 20-500 particles/mm². Especially particles in the size of 2-200 µm are available in this density. As indicated above, the channel ring or gliding, and the optional second gliding zone (see further below), have substantially no abrasive particles, or, as indicated above, especially 10% or less, more especially 5% or less, even more especially 1% or less of the number of abrasive particles comprised by the microdermabrasion zone. Hence, assuming e.g. the microdermabrasion zone having 250 particles of with one or more dimensions in the range of 100 µm per mm², the number of such particles at the gliding zone(s) may be in the range of 25/mm² or lower (respectively). The abrasive particles may e.g. be glued to a surface, to provide the microdermabrasion zone. However, alternative options are also possible. An abrasive surface can be made in many ways. Abrasive particles may be glued or metal plated. An abrasive structure can also be made from a solid material by machining or sanding a material. A surface treatment by a laser is also possible. Also by inject molding an abrasive surface can be created.

In an embodiment, the microdermabrasion zone is stationary, i.e. especially the microdermabrasion zone is not configured to move relative to the device. In yet another embodiment, the microdermabrasion zone may be able to move. For instance, the device may be configured to let the microdermabrasion zone vibrate. Optionally or additionally, the device may be configured to let the microdermabrasion zone rotate. Such rotation may also include a vibration movement, for instance when the rotation is only a small rotation hence and forth.

Especially, the channel rim may facilitate gliding of the device tip over a skin. The channel rim may therefore comprise a gliding zone or be considered the gliding zone. When moving over the skin of a human, the channel rim has a lower adhesive friction than the abrasive zone. For instance, the adhesive friction of the channel rim over the skin of a human may be less than 70% of the adhesive friction of the abrasive zone, especially less than 50%, even more especially less than 25%. When the conditions are the same, an (average) quotient of the adhesive friction of the channel rim over the adhesive friction of the abrasion zone will be (in average) 0.7 or lower, such as 0.25 or lower. As humans, especially males or females in the age of 20-45 are chosen, especially females, and especially the skin is the skin of a cheek, after cleaning and drying. Measurements are done at room temperature. For reference purposes, an example of how measurements can be performed is described in Hendriks et al., "Influence of Surface Roughness Material and Climate Conditions" (2010) Tribology Letters Vol. 37 (2) 361-373. Hence, the channel rim is especially a gliding zone and will have substantially no abrasive properties (in contrast to the microdermabrasion zone).

Abrasion (or abrasivity) may for instance also be measured with an abrasion tester. As will be clear to a person skilled in the art, the gliding zone(s) will have a substantially lower abrasion value (if measurable), such as especially 10% or less, more especially 5% or less, even more especially 1% or less than the abrasion value for the microdermabrasion zone.

In an embodiment, the channel rim or gliding zone is stationary, i.e. especially the gliding zone, is not configured to move relative to the device. In yet another embodiment, the gliding zone may be able to move. For instance, the device may be configured to let the gliding zone vibrate. Optionally or additionally, the device may be configured to let the microdermabrasion zone rotate. Such rotation may also include a vibration movement, for instance when the rotation is only a small rotation hence and forth. For instance, vibration of the gliding ring (gliding zone) may further facilitate gliding over the skin.

With such MDA device, at least part of the stratum corneum can be removed from the skin of a human. This can be done in a non-therapeutical treatment, such as a cosmetic treatment. Hence, the invention also provides a method for the controlled removal of at least part of the stratum corneum, the method comprising contacting the microdermabrasion device as defined herein with part of a skin and removing at least part of the stratum corneum while applying a vacuum to the vacuum channel. An advantage of the method and device of the invention is also that it (they) can be used for reducing a lateral force (gliding force) that has to be applied by a user when removing at least part of the stratum corneum with said device. Alternatively or additionally, the method and/or device as described herein can be used for reducing lateral force (gliding force) when removing at least part of the stratum corneum with said device. Further, alternatively or additionally, the method and/or device as described herein can be used for reducing a lateral force that has to be applied by a user when removing at least part of the stratum corneum with said device. Alternatively or additionally, the method and/or device as described herein can be used for increasing the treatment efficiency while not substantially increasing the vacuum level, keeping the same vacuum level, or even reducing, the vacuum level. Alternatively or additionally, the method and/or device as described herein can be used for increasing the treatment are while not substantially increasing, or even reducing, the gliding force. In yet a further aspect, the device and method may also be used in or for a therapeutic treatment.

In yet a further embodiment the microdermabrasion device as described herein further comprises a second gliding zone perimetrically surrounding the microdermabrasion zone. This second gliding zone may have a ring shape, which may substantially be round. However, the second gliding zone may also have a distorted ring shape, such as an elliptical ring shape (oval). Also other shapes may be possible, like a non-circular or non-oval shape. However, especially, the entire microdermabrasion zone is over its entire perimeter surrounded with such second gliding zone. Between the microdermabrasion zone and the second gliding zone, there may be a recession. However, the second gliding zone may also be directly adjacent to the microdermabrasion zone. The second gliding zone may be at equal height as the microdermabrasion zone, but may also be at lower or higher height. The second gliding zone is especially configured to gliding over the skin. Hence, in use the user may slide the device over the skin with the gliding zone, the microdermabrasion zone, and the second gliding zone in contact with the skin.

Likewise, as defined above with respect to the channel rim and the microdermabrasion zone, the second gliding zone will have no or substantially less abrasive properties when compared with the abrasion zone. In an embodiment, the quotient (in %) of the number of abrasive particles at the second gliding zone is especially 10% or less, more especially 5% or less, even more especially 1% or less of the number of abrasive particles comprised by the microdermabrasion zone, especially 0.1% or less. In an embodiment, such abrasive particles are not comprised at all by the second gliding zone. The lower content or absence of such particles by the second gliding zone may facilitate gliding. The numbers given here as especially provided as an indication for certain embodiments to indicate the difference between the functionality of the second gliding zone and the microdermabrasion zone. Hence, gliding zone(s) is (are) especially configured to facilitated gliding over the skin and the microdermabrasion zone is especially configured to abrade the skin (see also above).

The terms "upstream" and "downstream" relate to an arrangement of items or features relative to the propagation of the fluid, with in general upstream being at a higher pressure and downstream being at a lower pressure.

The term "substantially" herein, such as in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially the relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterising features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawings in which corresponding reference symbols indicate corresponding parts, and in which.

The drawings are not necessarily on scale.

Figure 3A:
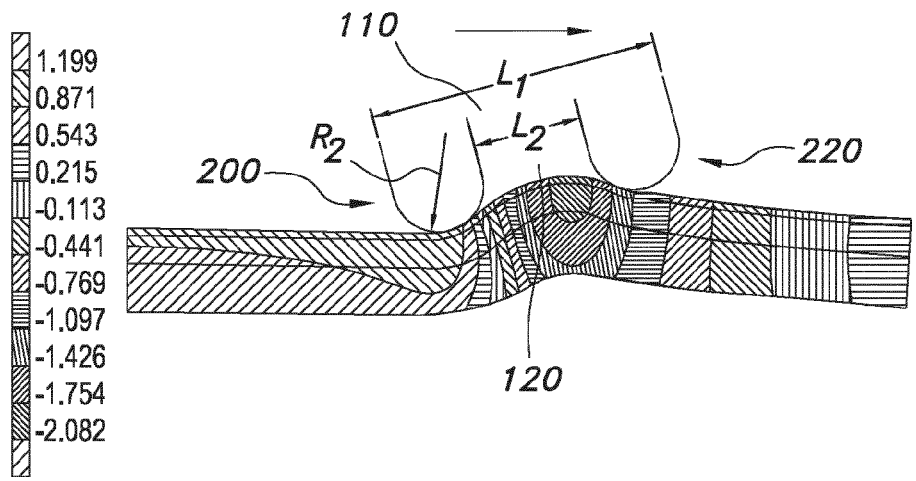
Figure 3B:
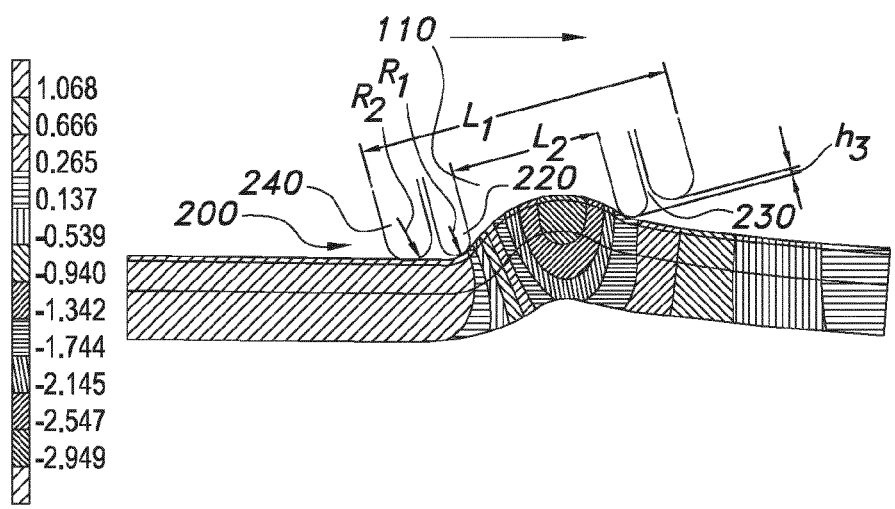

FIGS. 3a-3b compare skin vertical displacement (in mm) of the configurations with a separate gliding zone and abrasion zone (3b), with those wherein those zones are combined in one (3a).

DETAILED DESCRIPTION OF THE EMBODIMENTS

Figure 1A:
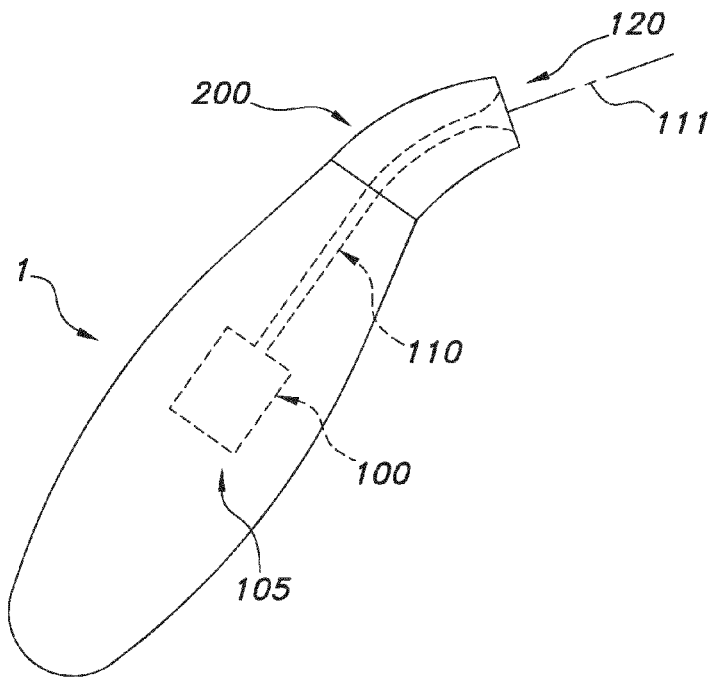
FIGS. 1a-1e schematically depict some aspects of the MDA device.
Figure 1B:
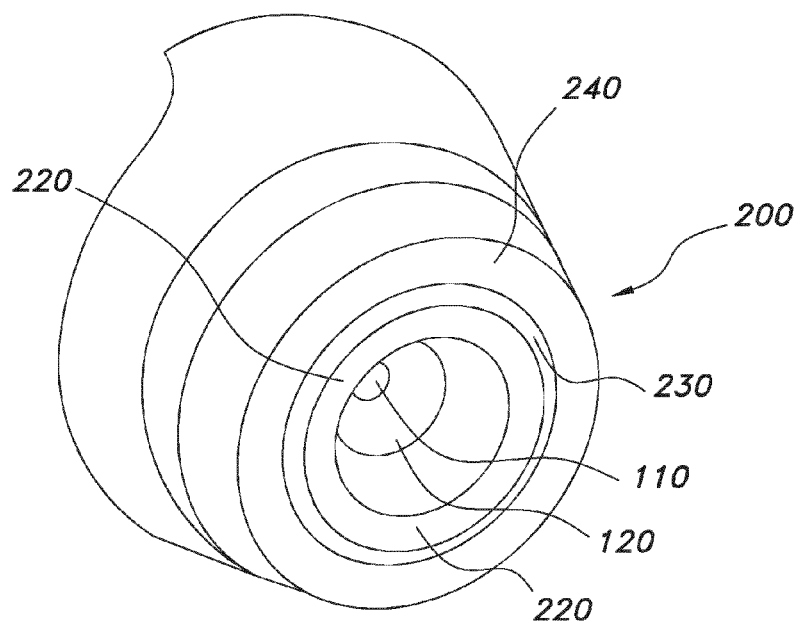

FIGS. 1a and 1b schematically depicts an embodiment of a microdermabrasion device 1. This device 1 comprises a vacuum system 100, with a pump 105 and a channel 110. Further, this device 1 comprises a device tip 200. Pump 105 can suck air into the channel 110. Channel 110 has a channel inlet 120 at the device tip 200. In other words, the device tip has a channel inlet 120 which is part of the channel 110 of the vacuum system 100. The channel inlet 120 is (perimetrically) surrounded by a channel rim 220. This channel rim 220 may facilitate gliding of the device tip 200 over a skin (not shown). The device tip 200 further comprises a microdermabrasion zone 240 configured remote from the channel inlet 120 with a recession 230 configured between the microdermabrasion zone 240 and the channel rim 220. FIG. 1b schematically depicts in 3D view by way of example an embodiment of a device tip 200 having a ring-shaped channel rim 220, recession 230 and abrasion zone 240, all (perimetrically) surrounding the channel inlet 120, but the recession 230 remote from the channel rim 220 and the abrasion zone 240 remote from the channel rim 220 and recession 230. Reference 111 indicates a (virtual) channel axis. The microdermabrasion zone 240 may include abrasive structures (not depicted), which are known per se.

Figure 1C:
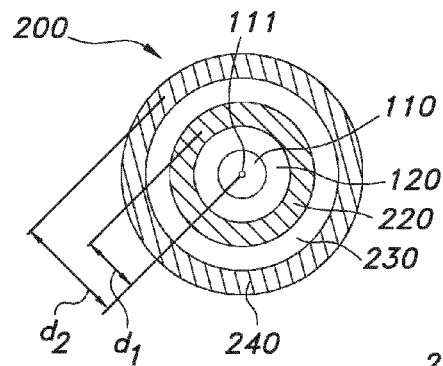
Figure 1D:
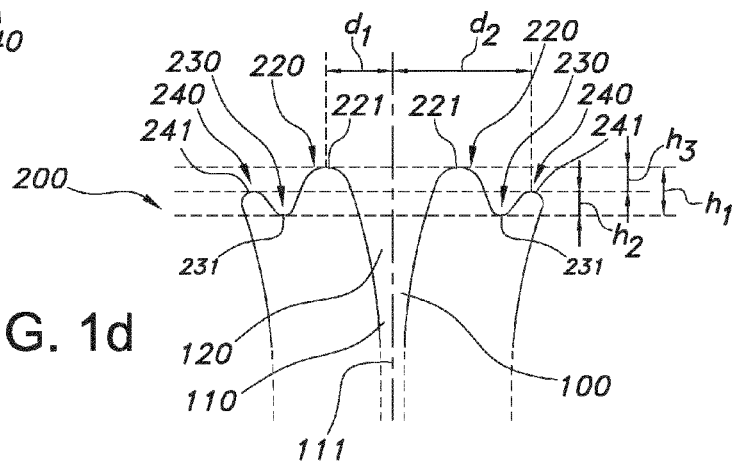

FIG. 1c schematically show a top view. The distance from the (top of the) channel rim 220 to the channel axis 111 is indicated with d1, and the distance from the (top of the) abrasion zone 240 is indicated with d2, with d2>d1. FIG. 1d schematically depicts a cross-sectional view. Here, wherein the channel rim 220 has relative to the recession bottom 231 a channel rim height h1. Further, the microdermabrasion zone 240 has relative to the recession bottom 231 a microdermabrasion zone height h2. For instance, the channel rim height h1 and the microdermabrasion zone height h2 have a height difference h3 in the range of 0-5 mm. Note that both the channel rim 220 (or gliding zone) and abrasion zone 240 in FIG. 1d are schematically depicted as having a curvature in a direction of the channel axis. Such curved surfaces may be comfortable when performing the microdermabrasion method. The top of the rim 220 is indicated with reference 221; the top of the abrasion zone is indicated with reference 241.

The present invention is not limited to handheld devices but may also relate to split devices, i.e. for instance a device with a main part, especially for providing the vacuum, and a tube with an abrasive treatment part, that can be moved at least partly independent of the main part. The tube may be a flexible tube.

Figure 1E:
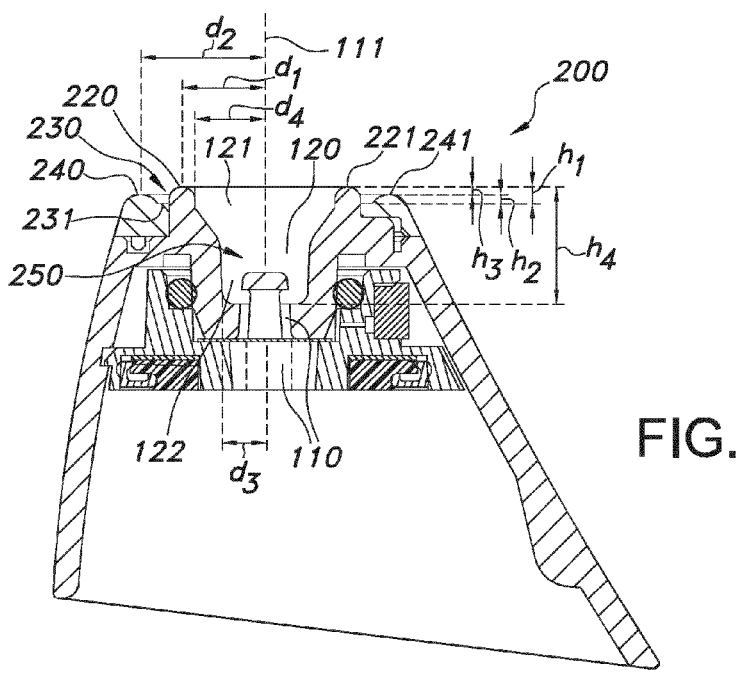

FIG. 1e schematically depicts a further variant. Reference 250 indicates a central element that may partly block the vacuum channel 110. Such central element 250 may protect the device from influx, for instance by accident, of a large piece. Further, this embodiment shows by way of example a channel inlet 120 having different dimensions over its length. An upper part or downstream part 121 is broader, and a lower part or upstream part (i.e. closer to a source of vacuum (not depicted) is more narrow. The distance from a channel axis to the wall of the channel inlet is indicated with references d4 and d3 respectively. Note that in case of a round rim 220 a round channel inlet), a round microdermabrasion zone 240, the references d1, d2, d3, d4 will be the same as the respective radii. In this schematic drawing, h4 indicates the height of the channel inlet or inlet zone. Characteristic values that may also apply to other embodiments described and/or depicted herein may be selected from the table below:

|    | mm          |    | mm   |
|----|-------------|----|------|
| h1 | >0; ≤10     | d1 | 3-30 |
| h2 | >0; ≤10     | d2 | 4-40 |
| h3 | −5-+5 (FIG. | d3 | 1-5  |

-continued

|    | mm                         |                      | mm   |
|----|----------------------------|----------------------|------|
|    | 1e about +0.2-1)           |                      |      |
| h4 | 3-15                       | d4 (1/2*L2; see      | 2-25 |
| R1 (see FIG. 3a/3b) | 0.3-5             | FIG. 3a/3b)          |      |
| R2 (see FIG. 3a/3b) | 0.3-5             |                      |      |

As indicated above, the above values may not only be applicable to the device schematically depicted in FIG. 1e. It appears that the microdermabrasion properties of devices with one or more of the above parameters may especially provide the above indicated properties. Further note that these values may, but do not necessarily implies a round rim, recession and microdermabrasion zone. One or more values may also vary over the height or width, including e.g. one or more of an oval rim or oval microdermabrasion zone.

Figure 2A:
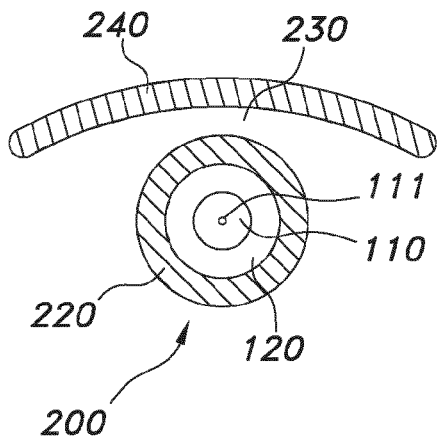
FIGS. 2a-2c schematically depict some configurations of the abrasion zone and channel rim.
Figure 2B:
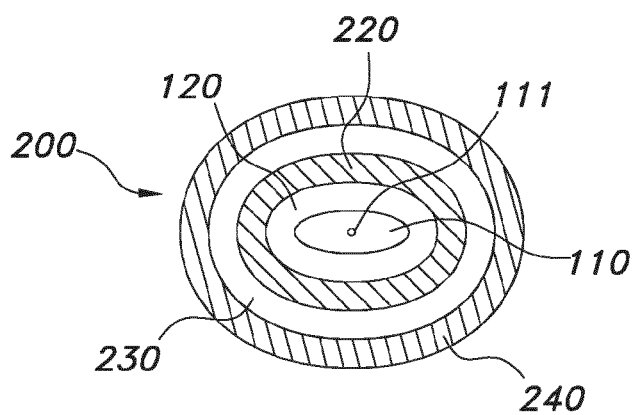

FIGS. 2a and 2b schematically depict, together with FIG. 1c, some possible variants of the channel rim 220 and abrasion zone 240, varying from circular zones (1c) to elliptical zones (2b), but also a circular channel rim but non-entirely (perimetrically) surrounding abrasion zone in FIG. 2a.

Figure 2C:
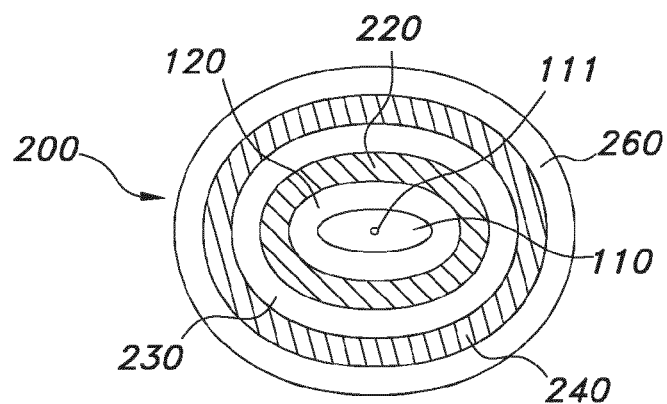

The microdermabrasion device 1 may further comprise a second gliding zone 260 perimetrically surrounding the microdermabrasion zone 240, as schematically depicted in FIG. 2c. Note that FIG. 2c shows an oval geometry, but the second gliding zone is not limited to such geometries. The second gliding zone 260 may also only partly surround the microdermabrasion zone 240 (see the analogous version for the microdermabrasion zone 240 and the channel rim 220 in FIG. 2a). In FIG. 2c, the second gliding zone is directly adjacent to the microdermabrasion zone 240, without a recession in between. However, a recession in between may also be possible. The top views of FIGS. 2a-2c do not show height differences between the gliding zone 220, the microdermabrasion zone 240, and the second gliding zone 260. However, there may be height differences.

FIGS. 3a-3b schematically depict the (vertical) displacement (in mm) on a virtual skin with a classical tip (3a) and with a tip as described herein. Hence, the invention can also be used for reducing a lateral force that has to be applied by a user when removing at least part of the stratum corneum with especially the herein described device. The lateral direction is indicated with the arrow. Reference R2 indicates the radius of the abrasive zone and L2 indicates the length between opposite parts of the channel inlet 120, especially channel rim 220. In case of a circular channel rim this may be the diameter. R1 in FIG. 3b indicates the radius of the channel rim. Reference L1 indicates the total width of the device tip 200.

In embodiments of the invention (see FIG. 3b), R1 may e.g. be in the range of 0.3-5 mm, such as 0.5-1 mm, and R2 may be in the range of 0.3-5 mm, such as 0.75-1.5 mm. L2 may e.g. be in the range of 4-50 mm, especially 5-12 mm, and L1 may be in the range of 8-80 mm, especially 12-25 mm. In systems without the separate channel rim 220 and microdermabrasion zone 240 with intermediate recession 230 (see FIG. 3a), L1 may e.g. be about 15 mm and L2 may be about 6 mm; the radius R2 may be about 2.25 mm.

Calculations that are the basis of FIGS. 3a-3b were done by finite Element Analysis. The behavior of a single ringed tip and a double ringed tip were investigated. The skin is modeled with three layers; an incompressible isotropic elastic fat layer, an incompressible anisotropic elastic dermal layer that takes into account the fiber orientation during stretching and an incompressible anisotropic elastic stratum corneum layer that takes into account the influence of its folds. The tip is assumed to be rigid compared to the skin. For the abrasive part an adhesive friction coefficient of 1.0 is assumed, for other tip parts 0.5. The tip is rotated to make skin contact. Observations of people using the device showed us that a tip, which is moved along the face is usually tilted. Therefore the tip was tilted. Vacuum levels of 0, 15, 25, 35 and 50 kPa were simulated.

Referring to FIGS. 1b, 1c, 1d, 1e, 2a, 2b, 2c and 3b, the microdermabrasion zone 240 may in embodiments be fixed (stationary). In such embodiments, the microdermabrasion zone 240 may not (be able to) move parallel or perpendicular to the channel axis 111. However, in other embodiments, the microdermabrasion zone 240 may be able to vibrate or rotate. For instance, the microdermabrasion zone 240 may vibrate in a direction (substantially) parallel to the channel axis. In embodiments, the height difference h3 may thus vary during use due to vibration. Other type of vibrations may also be possible. In embodiments, the microdermabrasion zone 240 may also be able to rotate, e.g. around the channel axis 111. In embodiments, the height difference h3 may be adjustable by the user.

An microdermabrasion device without the herein described microdermabrasion zone that perimetrically surrounds the rim (and recession) but for instance includes brushes appears to have less desirable properties and/or to be less flexible in choosing dimension and/or vacuum parameters. For instance, with brushes the vacuum may be higher for the same effect than with the device (and method) of the invention.

As indicated above, alternatively or additionally, also the channel rim or gliding zone 220 may be configured to more relative to the device. For instance, the device may be configured to vibrate the channel rim 220, by which friction may be reduced.

The invention claimed is:
1. A microdermabrasion device comprising:
   a vacuum system and
   a device tip,
   wherein the vacuum system comprises a channel with a channel inlet at the device tip,
   wherein the channel inlet is surrounded by a channel rim and has different dimensions over its length comprising a broader downstream portion and a relatively more narrow upstream portion, and
   wherein the device tip comprises a microdermabrasion zone including abrasive structures, configured remote from the channel inlet with a recession configured between the microdermabrasion zone and the channel rim,
   wherein the channel inlet is perimetrically surrounded by the channel rim, and
   wherein the microdermabrasion zone perimetrically surrounds the channel rim,
   wherein the channel rim comprises a gliding zone to facilitate gliding of the device tip over a skin,
   wherein the distance from the top of the channel rim to the channel axis is a distance d1 and the distance from the top of the microdermabrasion zone to the channel axis is a distance d2, where d2>d1, and
   wherein the channel rim has a height h1 relative to the recession bottom and the microdermabrasion zone has a height h2 relative to the recession bottom, where a height difference h3 is in the range of 0-5 mm wherein the channel rim height (h1) is larger than the microdermabrasion zone height (h2).

2. The microdermabrasion device according to claim 1, wherein the channel rim has a round ring shape, wherein the recession has a round ring shape, and wherein the microdermabrasion zone has a round ring shape.

3. The microdermabrasion device according to claim 1, wherein the channel rim has an oval ring shape, wherein the recession has an oval ring shape, and wherein the microdermabrasion zone has an oval ring shape.

4. The microdermabrasion device according to claim 1, wherein the channel rim height (h1) and the microdermabrasion zone height (h2) have a height difference (h3) in the range of up to 3 mm.

5. The microdermabrasion device according to claim 1, having a vacuum area in the range of 10-400 mm$^2$.

6. The microdermabrasion device according to claim 1, wherein the device is configured to provide a negative pressure in the range of 5-80 kPa.

7. The microdermabrasion device according to claim 1, having a vacuum area in the range of 45-75 mm$^2$ and wherein the device is configured to provide a negative pressure in the range of 15-60 kPa.

8. The microdermabrasion device according to claim 1, wherein microdermabrasion zone comprises abrasive structures attached to the microdermabrasion zone having mean dimensions in the range of 2-300 μm.

9. The microdermabrasion device according to claim 1, having a quotient of the adhesive friction of the channel rim over the adhesive friction of the abrasion zone of 0.7 or lower.

10. The microdermabrasion device according to claim 1, further comprising a second gliding zone perimetrically surrounding the microdermabrasion zone.

* * * * *